(12) United States Patent
Delaney et al.

(10) Patent No.: US 10,168,770 B2
(45) Date of Patent: *Jan. 1, 2019

(54) VIRTUAL REALITY SENSORY CONSTRUCT

(71) Applicant: International Business Machines Corporation, Armonk, NY (US)

(72) Inventors: John V. Delaney, Kildalkey (IE); Maeve M. O'Reilly, Rathdrum (IE); Niamh Phelan, Newbridge (IE); Claus Schroeder-Hansen, Copenhagen (DE); Niambh Scullion, Glasnevin (IE); Clea A. Zolotow, Key West, FL (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/964,339

(22) Filed: Apr. 27, 2018

(65) Prior Publication Data

US 2018/0246564 A1 Aug. 30, 2018

Related U.S. Application Data

(63) Continuation of application No. 15/404,385, filed on Jan. 12, 2017, which is a continuation-in-part of application No. 15/230,704, filed on Aug. 8, 2016.

(51) Int. Cl.
*G06F 3/01* (2006.01)
*G06F 3/03* (2006.01)
(Continued)

(52) U.S. Cl.
CPC .............. *G06F 3/011* (2013.01); *A61B 5/00* (2013.01); *G02B 27/017* (2013.01); *G06F 3/016* (2013.01);
(Continued)

(58) Field of Classification Search
CPC ....... A61B 2505/09; A61B 5/00; A61B 5/112; A61B 5/1128; A61B 5/45; A61B 5/4836;
(Continued)

(56) References Cited

U.S. PATENT DOCUMENTS 5,860,811 A 1/1999 Henderson
6,063,044 A 5/2000 Leonard et al.
(Continued)

FOREIGN PATENT DOCUMENTS

CN 102125436 A 7/2011
EP 2457501 A1 5/2012
(Continued)

OTHER PUBLICATIONS

P. Mell et al., "The NIST Definition of Cloud Computing", National Institute of Standards and Technology, Information Technology Laboratory, Sep. 2011, pp. 1-7.
(Continued)

*Primary Examiner* — Tony Davis
(74) *Attorney, Agent, or Firm* — Law Office of Jim Boice

(57) ABSTRACT

A tactile device for correcting biomechanical abnormalities using physical virtual reality simulations includes an outer hollow sphere, a pliable inner hollow sphere, a plurality of actuators, and a framework. The plurality of actuators physically couple the outer hollow sphere to the pliable inner hollow sphere, and are configured to reshape the pliable inner hollow sphere as the outer hollow sphere and the pliable inner hollow sphere rotate. The framework includes a plurality of powered rollers which support the outer hollow sphere and control a rotational speed and direction of the outer and inner spheres. A set of pressure sensors detect pressure applied by a user against the pliable inner hollow sphere as the user moves within. One or more processors determine a biomechanical abnormality in the user based on (Continued)

pressure readings from the pressure sensors. A sphere controller then modifies a physical configuration of the pliable inner hollow sphere.

20 Claims, 7 Drawing Sheets

(51) Int. Cl.
    *G06F 3/041*     (2006.01)
    *G02B 27/01*     (2006.01)
    *G06T 19/00*     (2011.01)
    *A61B 5/00*     (2006.01)
    *A61B 5/11*     (2006.01)

(52) U.S. Cl.
    CPC .......... *G06F 3/0304* (2013.01); *G06F 3/0414* (2013.01); *A61B 5/112* (2013.01); *A61B 5/1128* (2013.01); *A61B 5/45* (2013.01); *A61B 5/4836* (2013.01); *A61B 2505/09* (2013.01); *G06F 2203/012* (2013.01); *G06T 19/006* (2013.01)

(58) Field of Classification Search
    CPC . G02B 27/017; G06F 2203/012; G06F 3/011; G06F 3/016; G06F 3/0304; G06F 3/0414; G06T 19/006
    USPC .......................................................... 345/156
    See application file for complete search history.

(56) References Cited

U.S. PATENT DOCUMENTS

| | | | |
|---|---|---|---|
| 6,563,489 | B1 | 5/2003 | Latypov |
| 6,740,009 | B1 | 5/2004 | Hall |
| 2009/0156968 | A1 | 6/2009 | Sheradha |
| 2013/0184611 | A1 | 7/2013 | Nichols |
| 2017/0252642 | A1 | 9/2017 | Matina |
| 2018/0039325 | A1* | 2/2018 | Delaney ............... G06F 3/011 |
| 2018/0039330 | A1* | 2/2018 | Delaney ............... G06F 3/016 |

FOREIGN PATENT DOCUMENTS

| | | | |
|---|---|---|---|
| WO | 2002074167 | A1 | 9/2002 |
| WO | 2016105102 | A1 | 6/2016 |

OTHER PUBLICATIONS

Chang et al., "A Kinect-Based System for Physical Rehabilitation: A Pilot Study for Young Adults With Motor Disabilities". Research in Developmental Disabilities, vol. 32 (2011), pp. 2566-2570.

Frank Mokaya, "Acquiring Musculoskeletal Information in Active Environments, Suing a Wearable System". Adjunct Proceedings From the 2015 ACM International Joint Conference on Pervasive and Ubiquitous Computing and Proceddings of the 2015 ACM International Symposium on Wearable Computers, ACM, New York, 2015, pp. 453-458.

Hanley et al., "A Wireless Body Sensor Platform to Detect Progressive Deterioration in Musculoskeletal Systems". Scires, Advances in Internet of Things, vol. 3 (2013), pp. 53-63.

Anonymous, "Vendor Products: Cyberglove Systems". Virtalis, 2016. Web Sep. 8, 2016. <https://www.virtalis.com/blogs/products/cyberglove-systems/>.

Johansson et al., "Integration of Unsupervised Clustering, Interaction and Parallel Coordinates for the Exploration of Large Multivariate Data". IEEE, Proceedings of the Eighth International Conference on Information Visualization, Aug. 2004.

Anonymous, "What Is Seeme System?". Virtual Reality Kinect Rehabilitation, 2016. Web Sep. 8, 2016. <http://www.virtual-reality-rehabilitation.com/products/seeme/what-is-seeme>.

Han et al., "Motion Interfaces for Physical Therapy". Citris and the Banatao Institute, 2016. Web Sep. 8, 2016. <http://citris-uc.org/telehealth/project/motion-interfaces-physical-therapy/>.

Yu et al., "Motion Pattern Interpretation and Detection for Tracking Moving Vehicles in Airborne Video". Proceedings of the 2009 IEEE International Conference on Computer Vision and Pattern Recognition (CVPR), pp. 2671-2678.

Satya Prakash Mallick, "Feature Based Image Mosaicing". Department of Electrical and Computer Engineering, University of California, San Diego.

Susan Ann Richards, "4Motion". Justia, Trademarks, 2016. Web Jan. 12, 2017. <https://trademarks.justia.com/862/24/4motion-86224481.html>.

List of IBM Patents and Patent Applications Treated as Related. Apr. 26, 2018.

U.S. Appl. No. 15/230,704 Non-Final Office Action dated Apr. 4, 2018.

* cited by examiner

VIRTUAL REALITY SENSORY CONSTRUCT

BACKGROUND

The present disclosure relates to the field of computer systems, and specifically to computer systems that support virtual reality interfaces. More specifically, the present disclosure relates to augmenting visual virtual reality displays with tactile virtual reality outputs.

Virtual reality (VR) is an area of computer technology that creates a simulation of a physical world using immersive multimedia. This immersive multimedia provides outputs that are detected by a user's vision, hearing, and other senses, in order to give the user the illusion of experiencing a real physical world, rather than simply seeing and/or hearing a representation of the physical world.

While VR headsets provide visual immersion for gaming and other full-immersion experiences, current VR systems do not effectively support tactile sensations that involve the entire body of the user. That is, while a user can wear gloves and bodysuits that simulate touching an outside environment, such gloves/bodysuits provide very limited tactile sensations, due to the limited range of movement of tactile emulators (e.g., vibrating components, contracting components, etc.) found in such gloves/bodysuits. That is, while such gloves/bodysuits can emulate the feeling of a mild wave's motion, the user is not actually pushed around by the glove/bodysuit. Thus, the user never achieves a true simulation of movement/motion.

SUMMARY

In an embodiment of the present invention, a tactile device for correcting biomechanical abnormalities using physical virtual reality simulations includes an outer hollow sphere, a pliable inner hollow sphere, a plurality of actuators and a framework. The plurality of actuators physically couple the outer hollow sphere to the pliable inner hollow sphere and are configured to dynamically and physically reshape the pliable inner hollow sphere as the outer hollow sphere and the pliable inner hollow sphere rotate. The framework comprises a plurality of powered rollers which support the outer hollow sphere and control a rotational speed and direction of the outer hollow sphere and the pliable inner hollow sphere. A set of pressure sensors detect pressure applied by a user against the pliable inner hollow sphere as the user moves within the pliable inner hollow sphere as the outer hollow sphere and the pliable inner hollow sphere rotate. One or more processors determine a biomechanical abnormality in the user based on pressure readings from the pressure sensors as the user responds to movement of the pliable inner hollow sphere as the outer hollow sphere and the pliable inner hollow sphere rotate. A sphere controller then modifies a physical configuration of the pliable inner hollow sphere in order to treat the biomechanical abnormality in the user.

In an embodiment of the present invention, a tactile device for correcting biomechanical abnormalities using physical virtual reality simulations comprises an outer hollow sphere, a pliable inner hollow sphere, a plurality of actuators, and a framework. The plurality of actuators physically couple the outer hollow sphere to the pliable inner hollow sphere and are configured to dynamically and physically reshape the pliable inner hollow sphere as the outer hollow sphere and the pliable inner hollow sphere rotate. The framework comprises a plurality of powered rollers which support the outer hollow sphere and control a rotational speed and direction of the outer hollow sphere and the pliable inner hollow sphere. A camera captures visual images of the user as the user moves within the pliable inner hollow sphere as the outer hollow sphere and the pliable inner hollow sphere rotate. One or more processors determine a biomechanical abnormality in the user based on images from the camera as the user responds to the movement of the pliable inner hollow sphere as the outer hollow sphere and the pliable inner hollow sphere rotate. A sphere controller then modifies a physical configuration of the pliable inner hollow sphere in order to treat the biomechanical abnormality in the user.

In an embodiment of the present invention, a computer-implemented method controls a tactile device for correcting biomechanical abnormalities using physical virtual reality simulations. One or more processors transmit instructions to a plurality of powered rollers which support an outer hollow sphere that is physically coupled to a pliable inner hollow sphere by a plurality of actuators, where the pliable inner hollow sphere is occupied by a user, and where the instructions to the plurality of powered rollers control a rotational speed and direction of the outer hollow sphere and the pliable inner hollow sphere. The processor(s) transmit instructions to the plurality of actuators, where the instructions to the plurality of actuators cause the plurality of actuators to dynamically and physically reshape the pliable inner hollow sphere as the pliable inner hollow sphere rotates. From a camera, visual images are received of the user as the user moves within the pliable inner hollow sphere as the outer hollow sphere and the pliable inner hollow sphere rotate. From a set of pressure sensors, sensor readings are received that detect pressure applied by the user against the pliable inner hollow sphere as the user moves within the pliable inner hollow sphere as the outer hollow sphere and the pliable inner hollow sphere rotate. The processor(s) determine a biomechanical abnormality in the user based on images from the camera and pressure readings from the pressure sensors as the user responds to movement of the pliable inner hollow sphere as the outer hollow sphere and the pliable inner hollow sphere rotate. A sphere controller then modifies a physical configuration of the pliable inner hollow sphere in order to treat the biomechanical abnormality in the user.

DETAILED DESCRIPTION

Figure 1:
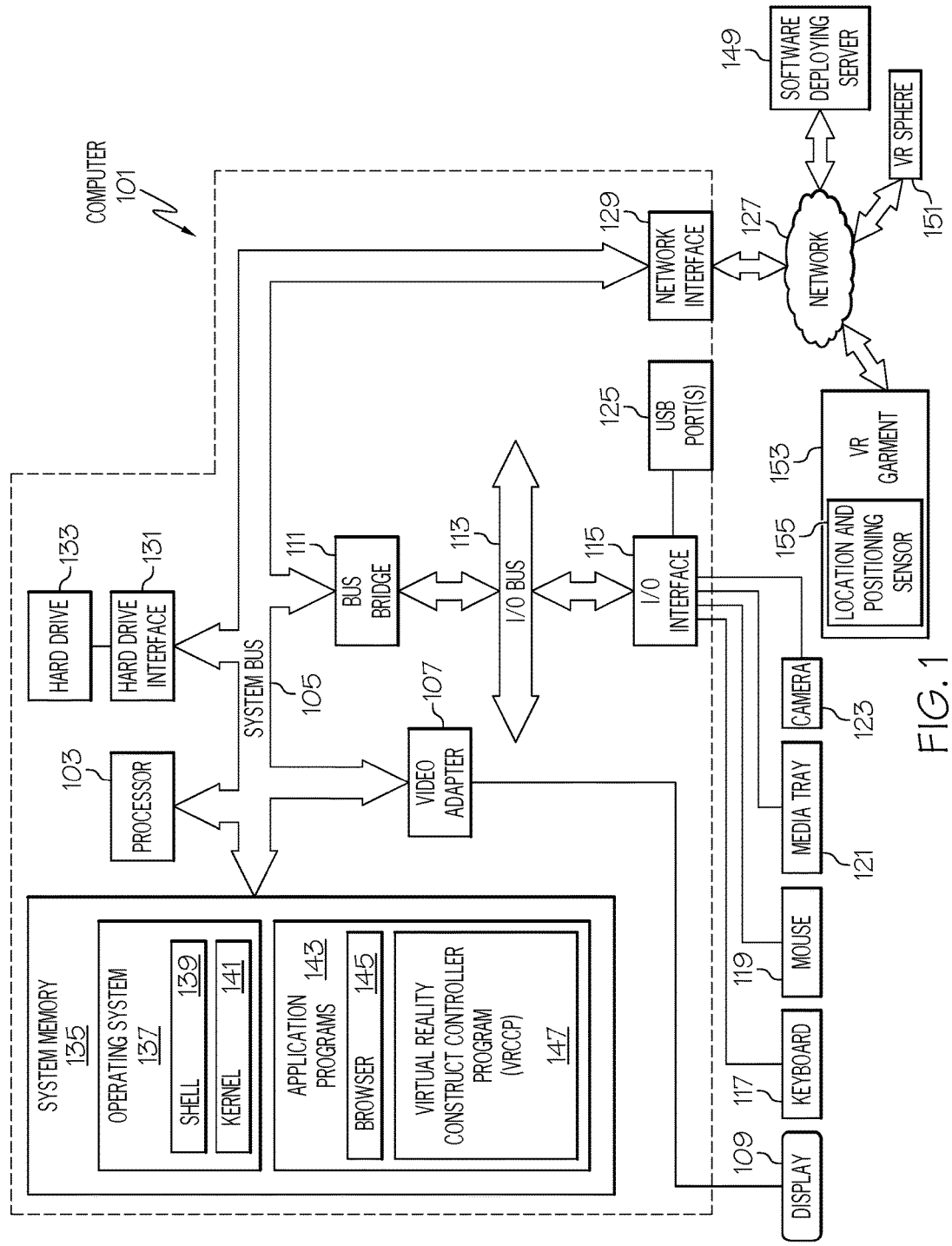
FIG. 1 depicts an exemplary system and network in which the present disclosure may be implemented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by software deploying server 149 and/or components in the virtual reality (VR) sphere 151 and/or the VR garment 153 shown in FIG. 1, and/or actuator 206 and/or control units 212a-212b shown in FIG. 2 and FIG. 4.

Exemplary computer 101 includes a processor 103 that is coupled to a system bus 105. Processor 103 may utilize one or more processors, each of which has one or more processor cores. A video adapter 107, which drives/supports a display 109 (which in one or more embodiments of the present invention is a touch-screen display capable of detecting touch inputs onto the display 109), is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a keyboard 117, a mouse 119, a media tray 121 (which may include storage devices such as CD-ROM drives, multi-media interfaces, etc.), a camera 123 (which in one or more embodiments is a digital camera capable of capturing still and/or moving visual images), and external USB port(s) 125. While the format of the ports connected to I/O interface 115 may be any known to those skilled in the art of computer architecture, in one embodiment some or all of these ports are universal serial bus (USB) ports.

As depicted, computer 101 is able to communicate with a software deploying server 149 and/or other devices/systems such as VR sphere 151 using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include a Virtual Reality Construct Controller Program (VRCCP) 147. VRCCP 147 includes code for implementing the processes described below, including those described in FIGS. 2-5. In one embodiment, computer 101 is able to download VRCCP 147 from software deploying server 149, including in an on-demand basis, wherein the code in VRCCP 147 is not downloaded until needed for execution. In one embodiment of the present invention, software deploying server 149 performs all of the functions associated with the present invention (including execution of VRCCP 147), thus freeing computer 101 from having to use its own internal computing resources to execute VRCCP 147.

Figure 2:
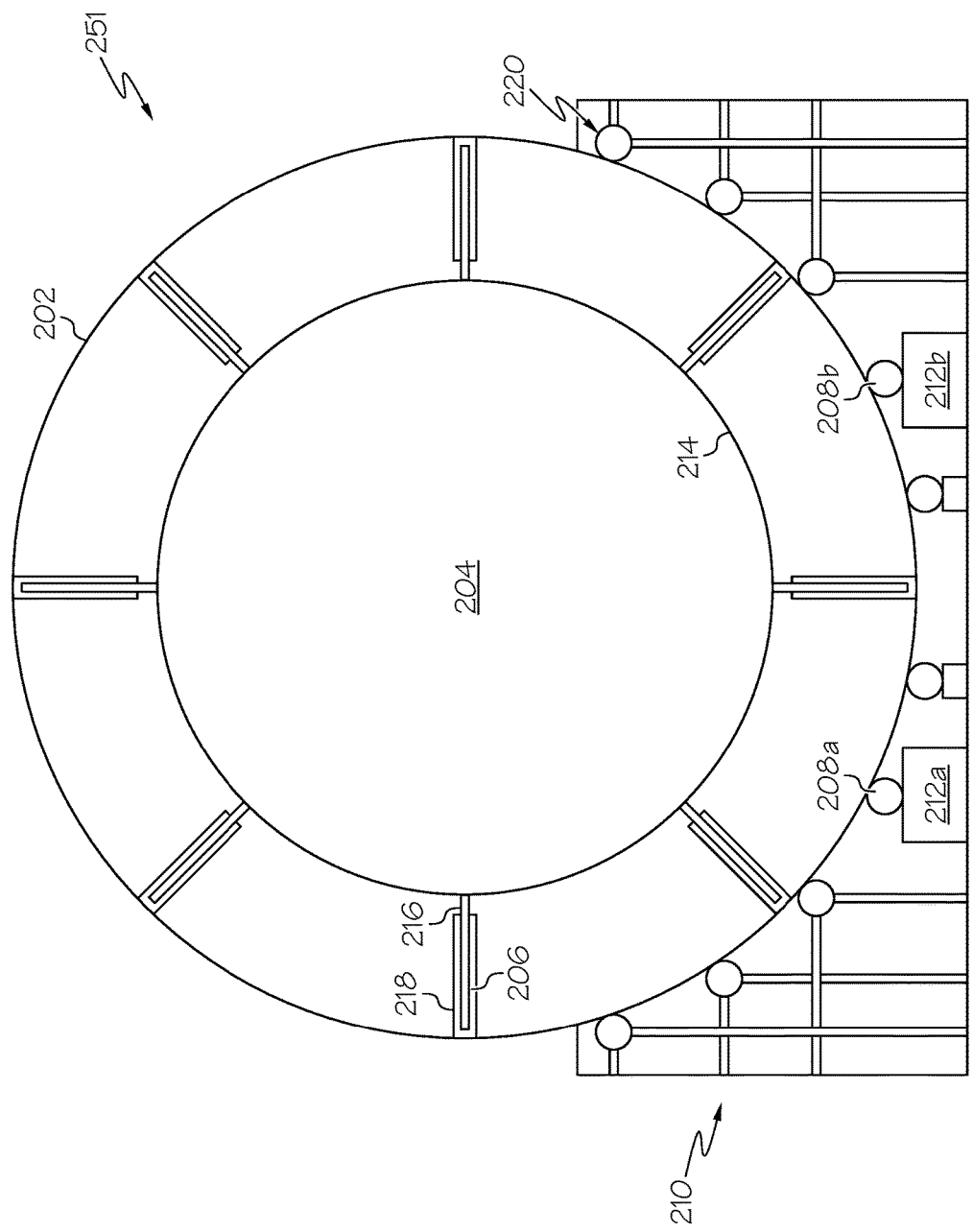
FIG. 2 illustrates a cross-sectional side view of a novel virtual reality (VR) sphere in accordance with one or more embodiments of the present invention, depicting the ability of the VR sphere to rotate along a first axis.
Figure 4:
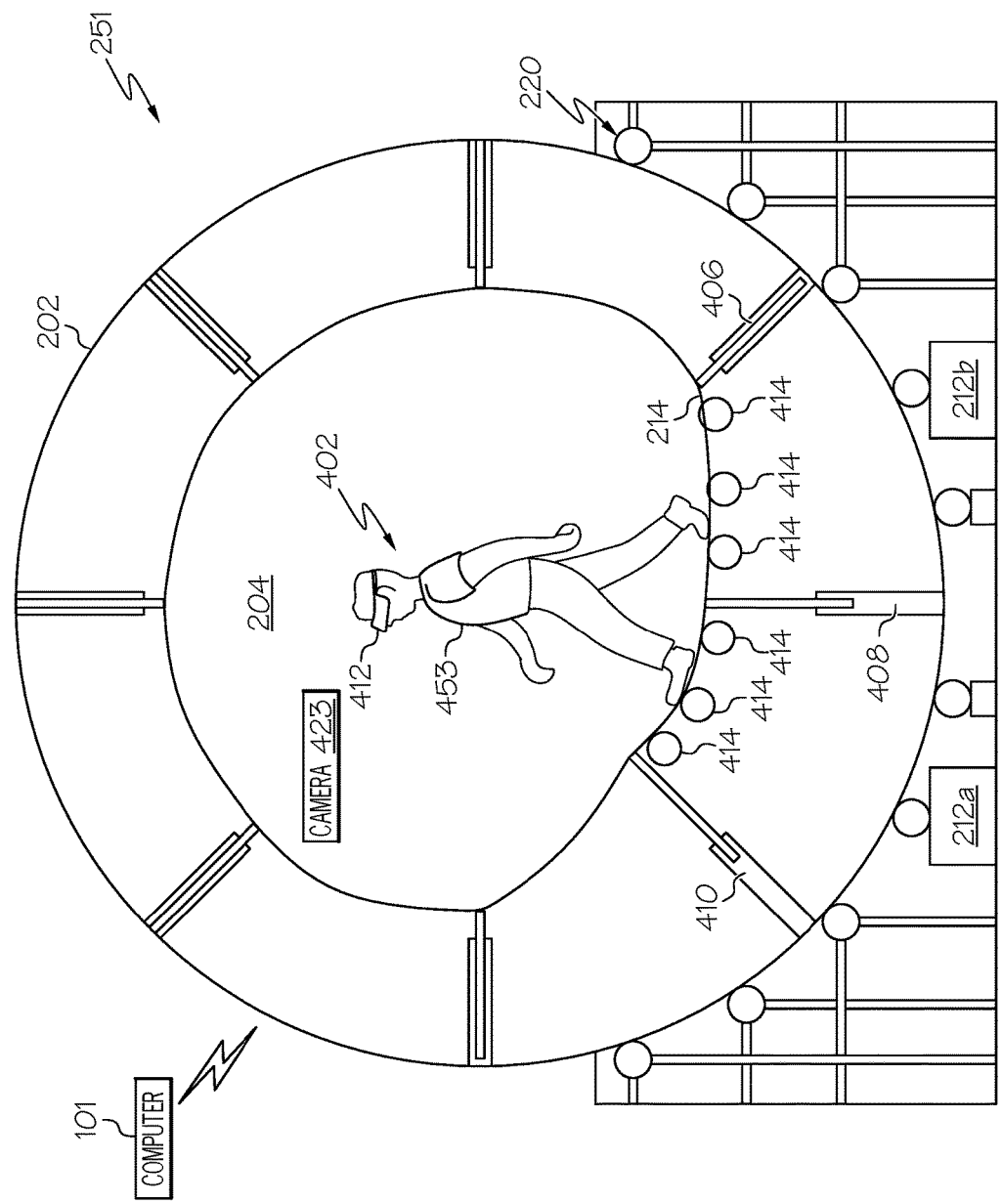
FIG. 4 illustrates a cross-sectional side view of the VR sphere shown in FIG. 2 depicting a user inside the VR sphere, and depicting actuators selectively changing a shape of an interior surface of the VR sphere in order to simulate irregular surfaces found in a physical world being simulated by the VR system.

Computer 101 is able to communicate with a virtual reality (VR) sphere 151, such as the VR sphere 251 depicted in FIG. 2, in order to control movement of the powered rollers (e.g., powered roller 208) that cause an outer hollow sphere 202 of the VR sphere 151 to rotate on one or more axes, as well as the movement of actuators (e.g., actuators 406, 408, 410 shown in FIG. 4 to manipulate the shape of the pliable inner hollow sphere 204 in the VR sphere 251).

Computer 101 is also able to communicate with a VR garment 153, which is a garment that is worn by a user to receive tactile, aural, and visual simulation inputs. That is, VR garment 153 is able to provide tactile sensations via vibrating components, visual sensations via a headset display, aural sensations via a headset speaker, etc., which provide a multimedia experience, to the user, which simulates a physical environment. VR garment 153 is also able to detect the location and three-dimensional real-time orientation of the user using a location and positioning sensor 155. For example, by using a series of electronic signals being transmitted within the VR sphere 151 and/or a set of electronic accelerometers, the location of the user within the VR sphere 151 and/or the physical orientation of the user (i.e., the position of the user's hands, legs, head, etc.) are determined in real time, thus providing computer 101 with the information needed to manipulate the flexible shape of the pliable inner hollow sphere 204 within the VR sphere 251.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

As described in one or more embodiments of the present invention, the presently presented novel VR sphere has as its base a rounded or half-sphere constructed so that it can change according to the VR program the person is interested in. For example, assume that the VR program is for climbing up a rock-climbing wall or riding downhill on a mountain bike. The present invention coordinates 1) the images and sounds being presented to the user via a headset and 2) the movement of the VR sphere with 3) a physical texture of the simulated surface (e.g., rocks, dips, crevices, etc. that would be encountered in a real version of the simulated surface as the user walks, climbs, bikes, etc.). This provides a unique improvement over the prior art by adding to the virtual reality immersion a true physical (not virtual) layer, which can morph to a specific game or task as required.

With reference then to FIG. 2, a cross-sectional side view of a novel virtual reality (VR) sphere 251 (analogous to VR sphere 151 shown in FIG. 1) in accordance with one or more embodiments of the present invention is presented.

VR sphere 251 has an outer hollow sphere 202 that is physically connected to a pliable inner hollow sphere 204 by multiple actuators, including the labeled actuator 206.

Outer hollow sphere 202 is constructed of a rigid material (e.g., metal) that 1) can be rotated through one or more axes (X,Y,Z in the Cartesian coordinate system) without deforming, breaking, cracking, etc., and 2) can support the actuators and the pliable inner hollow sphere 204 without deforming, breaking, cracking, etc.

Outer hollow sphere 202 rotates through one or more axes while being supported by rollers such as the depicted non-powered idler roller 220, and while being moved by powered rollers such as the depicted powered rollers 208a-208b. Thus, a control unit 212a receives instructions from computer 101 shown in FIG. 1 to turn powered roller 208a, thereby causing the outer hollow sphere 202 (and consequently the mechanically coupled pliable inner hollow sphere 204) to rotate. Similarly, a control unit 212b receives instructions from computer 101 shown in FIG. 1 to turn powered roller 208b, thereby also causing the outer hollow sphere 202 (and consequently the mechanically coupled pliable inner hollow sphere 204) to rotate. If powered roller 208a and powered roller 208b are aligned on different axes, then their rotation will cause the outer hollow sphere 202 to rotate on these different axes.

Pliable inner hollow sphere 204 is constructed of a pliable material that has enough ductile strength to handle shape changes and enough tensile strength to support the weight of a user standing inside the pliable inner hollow sphere 204 (see FIG. 4). Thus, pliable inner hollow sphere 204 may be constructed of flexible rubber, mesh-impregnated fibers, etc.

Actuators that control the shape of the pliable inner hollow sphere are mechanical devices that selectively extend and shorten. That is, when actuator 206 receives a signal from a controller (e.g., control unit 212a), an inner rod 216 will selectively be forced out of the actuator housing 218 of the actuator 206, or will be pulled back into the actuator housing 218 of the actuator 206. This movement of the inner rod 216 may be caused by applying a current to the actuator housing 218, thus creating an electromagnetic field that forces a magnetized inner rod 216 to move in or out of the actuator housing 218, depending on the direction of the applied current.

Alternatively, actuator 206 may be a pneumatic or hydraulic actuator, which pushes and pulls the inner rod out of and into the actuator housing 218 using air (pneumatic) or liquid (hydraulic) pressure.

The movement of the inner rods within the actuators causes the shape of the inner surface 214 to change in accordance with instructions to the actuators (e.g., processing logic within actuator 206) received from the controlling computer 101 (see FIG. 1) as the VR sphere 251 rotates along one or more axes (X,Y,Z). That is, as control unit 212a causes powered roller 208a to rotate the outer hollow sphere 202 in a certain direction, a user walking within the pliable inner hollow sphere 204 (see FIG. 4) will encounter (e.g., walk on) different regions of the inner surface 214 of the pliable inner hollow sphere 204. These different regions will have their shapes changed to comport with the virtual image being seen by the user while walking within the pliable inner hollow sphere 204. While only a few actuators are depicted in FIG. 2 for purposes of simplicity, it is understood that in practice there will be numerous actuators (more than 1 actuator per 10 cm square on the inner surface 214), thus providing a high degree of tactile/shape resolution.

Figure 3:
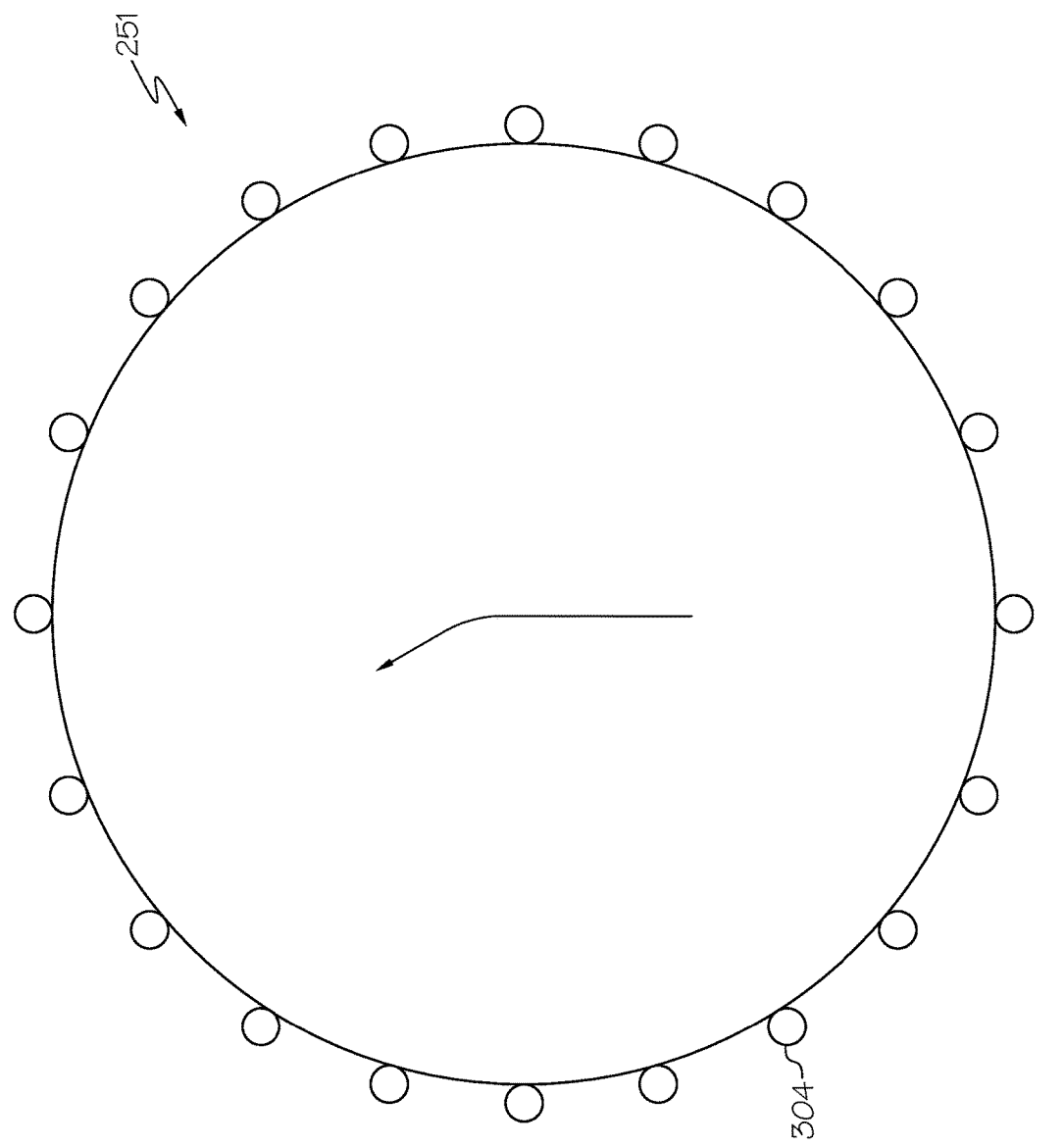
FIG. 3 depicts a cross-sectional top view of the VR sphere shown in FIG. 2 in accordance with one or more embodiments of the present invention, illustrating an ability to change a yaw along a second axis.

While the VR sphere 251 shown in FIG. 2 is depicted as rotating along one axis, it is to be understood that VR sphere 251 can rotate in various axes in accordance with one or more embodiments of the present invention. For example, as shown in FIG. 3, VR sphere 251 is able to rotate along another axis (e.g., can change its yaw along a second axis) by activating a powered roller 304 found in this other axis. Similarly, other powered rollers (not depicted) in other axes can cause VR sphere 251 to rotate through one or more of the other 3-axes.

With reference now to FIG. 4, a cross-sectional side view of the VR sphere shown in FIG. 2 depicts a user inside the VR sphere 251, and depicts actuators selectively changing a shape of an interior surface of the VR sphere in order to simulate irregular surfaces found in a physical world being simulated by the VR system. Note that the changes to the inner surface 214 themselves are physical, not simulated or virtual. However, while the user 402 is wearing a VR headset 412, he/she will see an image (created by wireless signals sent from computer 101 under the direction of a VR program) of a physical world (e.g., a climbing wall). As the VR sphere 251 rotates (under the direction of instructions transmitted from the computer 101), the user 402 "climbs" along the inner surface 214. While the user moves along the inner surface 214, the computer 101 coordinates activation of the actuators shown in FIG. 4, thus changing the actual (not virtual) geometry of the inner surface 214, which the user may physically touch/grab, thus giving the real physical sensation of grabbing physical objects (e.g., handholds on the climbing wall) that correspond with 1) the image being projected to the user's eyes by the VR headset 412 and 2) the movement/rotation of the VR sphere 251 (as controlled by control units 212a-212b to move the rollers that rotate the VR sphere 251).

For example, assume that user 402 is walking inside of the rotating VR sphere 251. Assume further that the VR program being run by computer 101 simulates walking over rocky terrain. As such, when the user walked across the inner surface 214 of the pliable inner hollow sphere 204 that is in contact with actuator 406, the inner surface 214 would be depressed, since actuator 406 is retracted. However, when user 402 reaches that area on the inner surface 214 that is in contact with actuator 408, the inner surface 214 rises somewhat, since the actuator 408 is partially extended. Furthermore, when user 402 reaches that area on the inner surface 214 that is in contact with actuator 410, the inner surface 214 rises even more, since the actuator 408 is fully extended.

Thus, as depicted in FIGS. 2-4, in one or more embodiments of the present invention a tactile device (e.g., VR sphere 251) for virtual reality simulations includes an outer hollow sphere (e.g., outer hollow sphere 202), a pliable inner hollow sphere (e.g., pliable inner hollow sphere 204), a plurality of actuators (e.g., actuators 406, 408, 410 and other unlabeled actuators depicted in FIG. 4), and a framework (e.g., framework 210 shown in FIG. 2) that has multiple rollers, both powered rollers (e.g., powered rollers 208a-208b shown in FIG. 2) for rotating the VR sphere as well as unpowered idler rollers (e.g., idler roller 220) for supporting the VR sphere.

As described herein, the plurality of actuators physically couple the outer hollow sphere to the pliable inner hollow sphere, and are configured to dynamically and physically reshape the pliable inner hollow sphere as the outer hollow sphere and the pliable inner hollow sphere rotate.

As described herein, the plurality of powered rollers also support the outer hollow sphere, and control a rotational speed and direction of the outer hollow sphere and the pliable inner hollow sphere.

As depicted in exemplary FIG. 4, in one or more embodiments of the present invention the plurality of actuators press against the pliable inner hollow sphere to create different shapes within the pliable inner hollow sphere that are encountered as a user moves within the pliable inner hollow sphere while the pliable inner hollow sphere rotates.

As described herein and in one or more embodiments of the present invention, an inner surface (e.g., inner surface 214) of the pliable inner hollow sphere is covered by a soft rubbery material, thus giving better tactile grip/sensation to the user.

In one or more embodiments of the present invention, the pliable inner hollow sphere has an inner diameter of at least one meter, such that a small child may stand up inside of the VR sphere.

In one or more embodiments of the present invention, the pliable inner hollow sphere has an inner diameter of at least two meters, such that a grown adult may stand up inside of the VR sphere.

As described herein and in one or more embodiments of the present invention, the plurality of actuators are electromechanical actuators.

As described herein and in one or more embodiments of the present invention, the plurality of actuators are pneumatic actuators.

As described herein and in one or more embodiments of the present invention, a camera 423 (analogous to camera 123 shown in FIG. 1) is capable of capturing movement images of user 402 as user 402 moves in response to the VR sphere 251 rotating and/or images being received via VR headset 412.

As described herein and in one or more embodiments of the present invention, pressure sensors 414 within or next to the inner surface 214 are able to detect the level of pressure exerted by the hands and/or feet and/or other body parts of user 402, in order to further determine what types of physical reactions/movements are exerted by user 402 in response to the VR sphere 251 rotating and/or images being received via VR headset 412.

Figure 5:
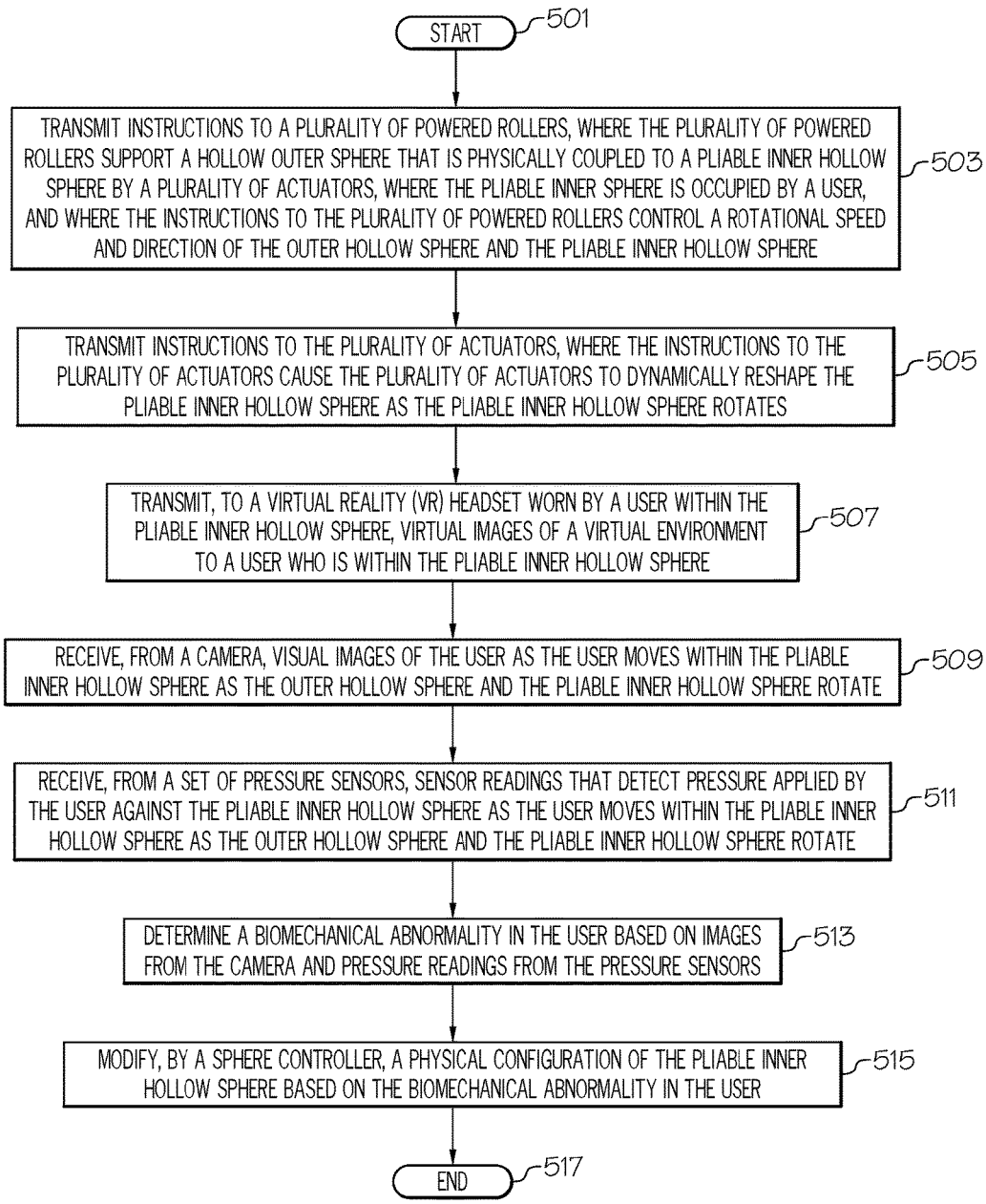
FIG. 5 is a high-level flow-chart of one or more steps performed by one or more processors and/or other hardware devices to modify a physical shape of the interior of the VR sphere shown in FIG. 4 based on user responses to earlier modifications to the physical shape of the interior of the VR sphere.

With reference now to FIG. 5, a high-level flow-chart of one or more steps performed by one or more processors and other hardware devices (including but not limited to the actuators depicted in FIG. 4) to detect biomechanical abnormalities of a user by modifying a physical shape of an interior of the VR sphere is presented.

After initiator block 501, one or more processors (e.g., from computer 101) transmit instructions to a plurality of powered rollers (e.g., powered rollers 208a-208b shown in FIG. 2), as described in block 503. As shown in the figures, the plurality of powered rollers support an outer hollow sphere (e.g., outer hollow sphere 202) that is physically coupled to a pliable inner hollow sphere (e.g., pliable inner hollow sphere 204) by a plurality of actuators (e.g., actuators 406, 408, 410). As shown in FIG. 4 the pliable inner hollow sphere is occupied by a user, and the instructions to the plurality of powered rollers control a rotational speed and direction of the outer hollow sphere and the pliable inner hollow sphere.

As described in block 505, the processor(s) transmit instructions to the plurality of actuators that cause the plurality of actuators to dynamically reshape the pliable inner hollow sphere as the pliable inner hollow sphere rotates.

As described in block 507, a computer (e.g., a sphere controller such as computer 101 shown in FIG. 4) transmits, to a virtual reality (VR) headset (e.g., VR headset 412) worn by a user (e.g., user 402) within the pliable inner hollow sphere, virtual images of a virtual environment to the user. For example, the images displayed on the VR headset may be of a climbing wall, a sidewalk, an obstacle course, etc.

As described in block 509, a computer receives, from a camera (e.g., camera 423), visual images of the user as the user physically moves within the pliable inner hollow sphere as the outer hollow sphere and the pliable inner hollow sphere rotate, as well as sensor readings from a set of pressure sensors (e.g., pressure sensors 414) that detect pressure applied by the user against the pliable inner hollow sphere as the user physically moves within the pliable inner hollow sphere as the outer hollow sphere and the pliable inner hollow sphere rotate (see block 511 in FIG. 5).

One or more processors (e.g., within computer 101) then determine a biomechanical abnormality in the user based on images from the camera and pressure readings from the pressure sensors as the user responds to the virtual images of the virtual environment and movement of the pliable inner hollow sphere as the outer hollow sphere and the pliable inner hollow sphere rotate, as described in block 513 in FIG. 5. That is, if the user stumbles, limps, etc. in a manner that indicates a biomechanical abnormality (e.g., a medical condition, improper movement due to poor training, etc.), then the system will recognize this biomechanical abnormality.

As described in block 515, a sphere controller (e.g., computer 101 as shown in FIG. 4) will then modify a physical configuration of the pliable inner hollow sphere based on the biomechanical abnormality in the user. For example, if the user is favoring a certain side of his/her body, then the physical configuration of the pliable inner hollow sphere will be modified such that the user must exert more effort on that side of his/her body, in order to build up strength in that part of the user's body.

The flowchart ends at terminator block 517.

Thus, the device and/or method and/or computer program product presented herein improves on the prior art by giving the user an enhanced VR experience. That is, rather than simply seeing a simulated environment, with small physical sensations (e.g., as provided by vibrating or contracting components of a VR bodysuit or VR gloves), the present invention allows the user to physically feel dynamically changing shapes that are created as the VR sphere (within which the user is traversing) rotates.

As described herein and in one or more embodiments of the present invention, the plurality of actuators press against the pliable inner hollow sphere to create different shapes within the pliable inner hollow sphere that are encountered as the user moves within the pliable inner hollow sphere while the pliable inner hollow sphere rotates.

With the construct and the use of a virtual reality headset, the present invention thus allows users to be able to immerse themselves in an experience such as hiking a steep mountain path, with twist and turns, uneven footing and walk along, twisting and turning with the footpath, climbing up and down as the foot path moves along the elevations of the terrain. The control units and the rollers control the direction of roll inside the sphere, thus ensuring that the user experience includes directional changes (which is impossible with a treadmill).

While described herein in the context of recreation/gaming, the present invention is also useful to subject matter experts (SMEs) when examining simulated subject matters. For example, assume that the SME is a geological engineer, and that the VR program has data describing the shape of rocks and/or ore found well below the surface of the earth (e.g., where the SME cannot physically go). The present system may be configured to change the inner surface of the VR sphere (inside of which the SME is standing), such that the SME (wearing a VR headset) is able to see a simulated image of the rocks/ore while simultaneously physically tactilely "feeling" these rocks/ore by touching the changing surface of the inner portion of the VR sphere (which is reshaped to mirror the shape of the rocks/ore).

The present invention provides many advantages over the prior art when used in various embodiments. That is, while described in the figures as a tool for exercising and training, the present invention may also be used for any active training required for a job, such as military training, marching band practice, etc., limited only by the instructions found in the VR program that is controlling the VR sphere.

Thus, and described herein and in one or more embodiments, the present invention utilizes cameras (e.g., camera 423 shown in FIG. 4) and sensors (e.g., pressure sensors 414 shown in FIG. 4) that are embedded in a physical virtual reality construct (e.g., VR sphere 251 along with computer 101 supporting VR headset 412 shown in FIG. 4) to detect musculoskeletal imbalances. The interpretation of the generated information gives medical and fitness professionals, as well as individuals, an extra tool to help diagnose imbalances. Based on these interpretations and/or diagnoses, the VR sphere 251 can be further modified in order to facilitate a rehabilitation plan for user 402 or to prevent an injury to user 402 from occurring in the first place by early detection of imbalances.

In today's sedentary lifestyle, where sustained postures like sitting at a desk and driving are the norm, injuries that originate in simple unchecked musculoskeletal imbalances are on the rise.

Physiotherapy and similar interventions are conventionally used to address existing issues, not as a preventative measure. Thus, one or more embodiments of the present invention provides a virtual reality construct (e.g., VR sphere 251) that has embedded cameras (e.g., camera 423) and sensors (e.g., pressure sensors 414) that move. These cameras and sensors capture information about the person (e.g., user 402) in the virtual reality construct (also referred to herein as a "construct", and exemplified as VR sphere 251).

One or more embodiments of the present invention utilize geometric interpretation data in a multi-dimensional capacity in a virtual reality construct. The interpretation of the information may allow early diagnosis of a medical condition and provide simplified targeted remediation. The present invention may be incorporated into a standard heath/well-being check.

For example, individuals can use the virtual reality construct to engage in a physical training program before undertaking a new challenge like marathon training. Similarly, in order to maintain body agility, where weaknesses put pressure on other parts of body and result in impacting mobility, the presently-described virtual reality construct can be modified to train certain parts of the person's body. Similarly, the virtual reality construct can be used to train the person's body when undergoing physiological changes that result from surgery, major weight loss, growth spurts, injury, etc.

As described herein, the present invention presents a virtual reality construct where the subtleties associated with muscle imbalances and/or other physiological/biomechanical abnormalities are easily and accurately measured and then ameliorated by the virtual reality construct. The multidimensional construct engages the user in an immersive range of test movements, thus allowing the construct to measure and adapt to a full range of the user's reactions to the movement of the VR sphere 251 as indicated by the user's muscular strain, weight distribution, balance, range of motion, etc. Once the biomechanical issue is identified, the construct (e.g., VR sphere 251) can engage the user in a targeted re-balancing program.

Thus, the present invention is non-invasive, since no biomedical sensors (e.g., electromyography—EMG sensors) are required to identify biomechanical problems of the user.

Furthermore, the presently-described physical three dimensional device (e.g., VR sphere 251) measures subtleties associated with detection and remediation based on all axes of movement of the user.

Further, the present invention provides a user with targeted feedback based on his/her own progress in negotiating movement across the inner surface 214 of the VR sphere 251.

The construct may be equipped with cameras, sensors and pressure pads as described herein. It may simulate range of activities such as, sitting, rock climbing, running, walking.

In an embodiment of the present invention, VR headset 412 provides visuals to instruct the user 402 in a prescribed sequence of movements or enhances the physical simulation with visual feeds that challenge physical reactions. For example, the images projected in the VR headset 412 to the user 402 may prompt the user to stand on one leg, stand on one leg on a raised object, etc.

In an embodiment of the present invention, the user is recorded engaging in these activities for future examination.

One or more embodiments of the present invention utilize image recognition to detect biomechanical abnormalities in the user, such as imbalances, stumbling, etc. For example, excessive movement of the hips while running may indicate lack of strength in some muscle groups. A head rotation in an upper stretch may indicate back restriction. As such, the user will be directed (e.g., from instructions provided by the VR headset 412) to perform activities that strengthen muscles, thus training the user's body to correct the detected imbalances. For example, if the user's imbalances/abnormalities are caused by poor upper body strength, the computer 101 may send the VR headset 412 an image of a rock climbing wall and may also adjust the configuration and movement of the inner surface 214 to physically emulate such a wall, thus building up the user's upper body strength.

The user may be recorded doing these activities and with the help of image detection software, anomalies (i.e., incorrect motion/movement, not activating the correct muscles) can be detected and remedial action, with the help of a medical professional, can be taken.

Thus, as described herein data from the sensors (e.g., captured visual images from camera 423 and/or captured pressure readings from pressure sensors 414) combined with a cognitive computer (e.g., computer 101) create, based on an understanding of the human body, a tentative diagnosis of a biomechanical anomaly (i.e., a physiological disease, weakness, etc. of the user 402). The computer 101 then modifies the configuration of the VR sphere 251 in order to induce certain remedial actions (e.g., new challenges to certain muscle groups of user 402).

The present invention may be implemented in one or more embodiments using cloud computing. Nonetheless, it is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
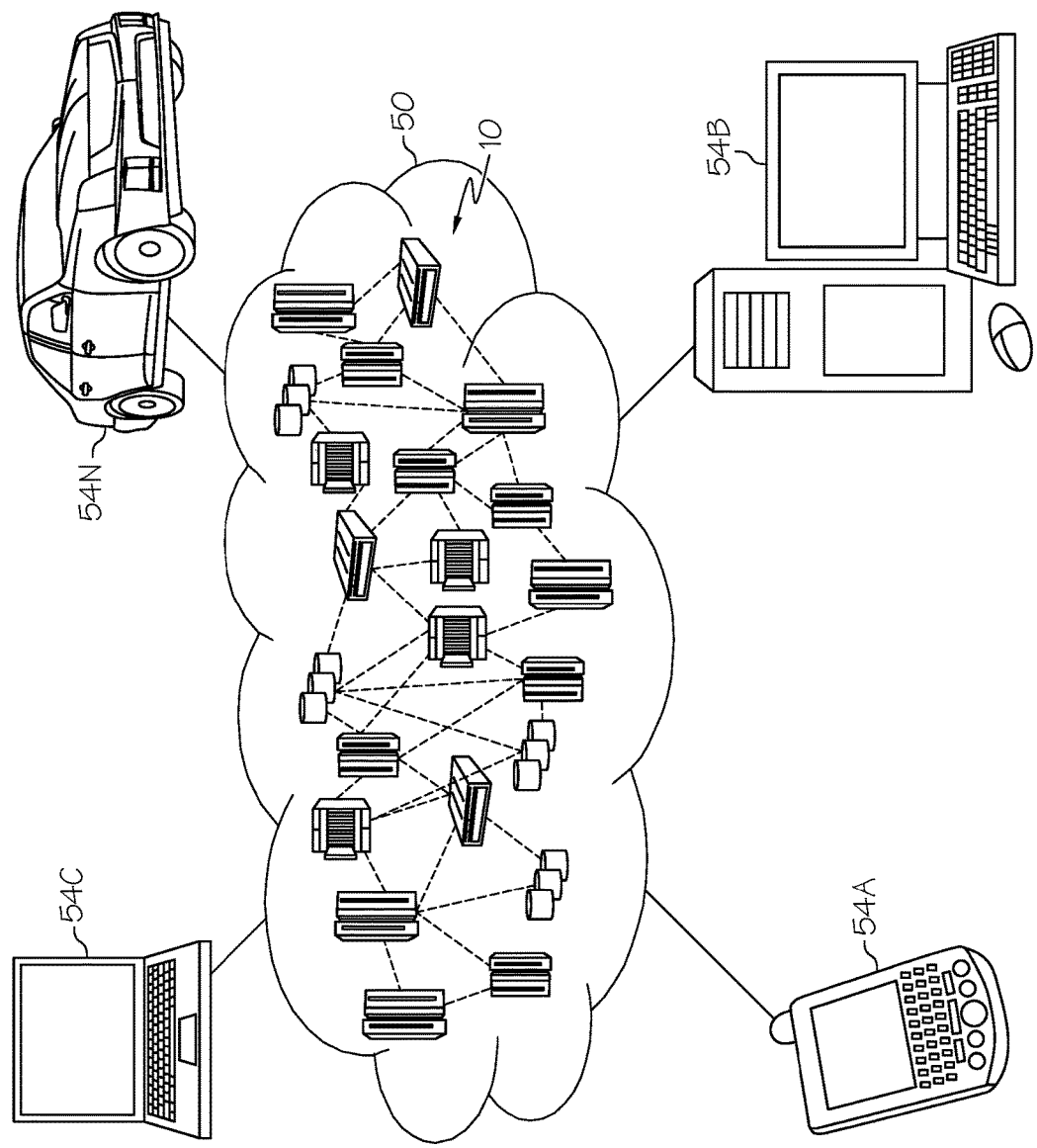
FIG. 6 depicts a cloud computing environment according to an embodiment of the present invention.

Referring now to FIG. 6, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-54N shown in FIG. 6 are intended to be illustrative only and that computing nodes 10 and cloud computing environment 50 can communicate with any type of computerized device over any type of network and/or network addressable connection (e.g., using a web browser).

Figure 7:
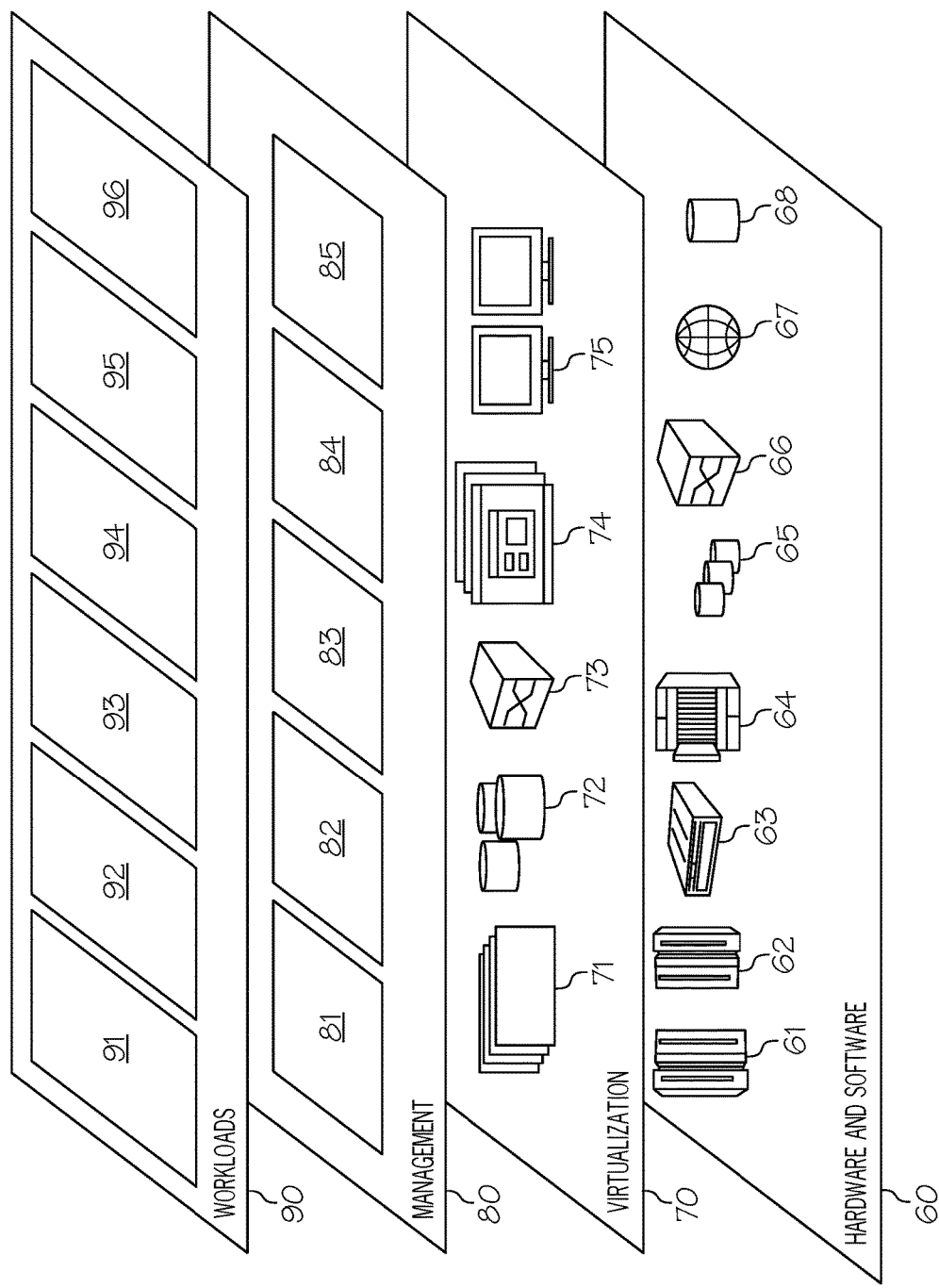
FIG. 7 depicts abstraction model layers of a cloud computer environment according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and virtual reality processing 96, which performs one or more functions described for the present invention.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A tactile device for correcting biomechanical abnormalities using physical virtual reality simulations, the tactile device comprising:
   an outer hollow sphere;
   a pliable inner hollow sphere;
   a plurality of actuators, wherein the plurality of actuators physically couple the outer hollow sphere to the pliable inner hollow sphere, and wherein the plurality of actuators are configured to dynamically and physically reshape the pliable inner hollow sphere as the outer hollow sphere and the pliable inner hollow sphere rotate;
   a framework comprising a plurality of powered rollers, wherein the plurality of powered rollers:
      support the outer hollow sphere, and
      control a rotational speed and direction of the outer hollow sphere and the pliable inner hollow sphere;
   a set of pressure sensors that detect pressure applied by a user against the pliable inner hollow sphere as the user moves within the pliable inner hollow sphere as the outer hollow sphere and the pliable inner hollow sphere rotate;
   one or more processors that determine a biomechanical abnormality in the user based on pressure readings from the pressure sensors as the user responds to movement of the pliable inner hollow sphere as the outer hollow sphere and the pliable inner hollow sphere rotate; and
   a sphere controller that modifies a physical configuration of the pliable inner hollow sphere in order to treat the biomechanical abnormality in the user.

2. The tactile device of claim 1, wherein the plurality of actuators press against the pliable inner hollow sphere to create different shapes within the pliable inner hollow sphere that are encountered as a user moves within the pliable inner hollow sphere while the pliable inner hollow sphere rotates.

3. The tactile device of claim 1, where an inner surface of the pliable inner hollow sphere is covered by a soft rubbery material.

4. The tactile device of claim 1, wherein the pliable inner hollow sphere has an inner diameter of at least one meter.

5. The tactile device of claim 1, wherein the plurality of actuators are electromechanical actuators.

6. The tactile device of claim 1, wherein the plurality of actuators are pneumatic actuators.

7. The tactile device of claim 1, wherein the tactile device is coupled to a computer that controls the plurality of actuators and the powered rollers.

8. A tactile device for correcting biomechanical abnormalities using physical virtual reality simulations, the tactile device comprising:
an outer hollow sphere;
a pliable inner hollow sphere;
a plurality of actuators, wherein the plurality of actuators physically couple the outer hollow sphere to the pliable inner hollow sphere, and wherein the plurality of actuators are configured to dynamically and physically reshape the pliable inner hollow sphere as the outer hollow sphere and the pliable inner hollow sphere rotate;
a framework comprising a plurality of powered rollers, wherein the plurality of powered rollers:
support the outer hollow sphere, and
control a rotational speed and direction of the outer hollow sphere and the pliable inner hollow sphere;
a camera for capturing visual images of the user as the user moves within the pliable inner hollow sphere as the outer hollow sphere and the pliable inner hollow sphere rotate;
one or more processors that determine a biomechanical abnormality in the user based on images from the camera as the user responds to the movement of the pliable inner hollow sphere as the outer hollow sphere and the pliable inner hollow sphere rotate; and
a sphere controller that modifies a physical configuration of the pliable inner hollow sphere in order to treat the biomechanical abnormality in the user.

9. The tactile device of claim 8, wherein the plurality of actuators press against the pliable inner hollow sphere to create different shapes within the pliable inner hollow sphere that are encountered as a user moves within the pliable inner hollow sphere while the pliable inner hollow sphere rotates.

10. The tactile device of claim 8, where an inner surface of the pliable inner hollow sphere is covered by a soft rubbery material.

11. The tactile device of claim 8, wherein the pliable inner hollow sphere has an inner diameter of at least one meter.

12. The tactile device of claim 8, wherein the plurality of actuators are electromechanical actuators.

13. The tactile device of claim 8, wherein the plurality of actuators are pneumatic actuators.

14. The tactile device of claim 8, wherein the tactile device is coupled to a computer that controls the plurality of actuators and the powered rollers.

15. A computer-implemented method comprising:
transmitting, by one or more processors, instructions to a plurality of powered rollers, wherein the plurality of powered rollers support an outer hollow sphere that is physically coupled to a pliable inner hollow sphere by a plurality of actuators, wherein the pliable inner hollow sphere is occupied by a user, and wherein the instructions to the plurality of powered rollers control a rotational speed and direction of the outer hollow sphere and the pliable inner hollow sphere;
transmitting, by one or more processors, instructions to the plurality of actuators, wherein the instructions to the plurality of actuators cause the plurality of actuators to dynamically and physically reshape the pliable inner hollow sphere as the pliable inner hollow sphere rotates;
receiving, from a camera, visual images of the user as the user moves within the pliable inner hollow sphere as the outer hollow sphere and the pliable inner hollow sphere rotate;
receiving, from a set of pressure sensors, sensor readings that detect pressure applied by the user against the pliable inner hollow sphere as the user moves within the pliable inner hollow sphere as the outer hollow sphere and the pliable inner hollow sphere rotate;
determining, by one or more processors, a biomechanical abnormality in the user based on images from the camera and pressure readings from the pressure sensors as the user responds to movement of the pliable inner hollow sphere as the outer hollow sphere and the pliable inner hollow sphere rotate; and
modifying, by a sphere controller, a physical configuration of the pliable inner hollow sphere in order to treat the biomechanical abnormality in the user.

16. The computer-implemented method of claim 15, wherein the plurality of actuators press against the pliable inner hollow sphere to create different shapes within the pliable inner hollow sphere that are encountered as the user moves within the pliable inner hollow sphere while the pliable inner hollow sphere rotates.

17. The computer-implemented method of claim 15, where an inner surface of the pliable inner hollow sphere is covered by a soft rubbery material.

18. The computer-implemented method of claim 15, wherein the pliable inner hollow sphere has an inner diameter of at least one meter.

19. The computer-implemented method of claim 15, wherein the plurality of actuators are electromechanical actuators.

20. The computer-implemented method of claim 15, wherein the plurality of actuators are pneumatic actuators.

* * * * *